(12) United States Patent
Linder et al.

(10) Patent No.: US 11,369,417 B1
(45) Date of Patent: Jun. 28, 2022

(54) MODULAR POLYAXIAL PEDICLE SCREW ASSEMBLY WITH SPLIT RING

(71) Applicant: Curiteva, Inc., Tanner, AL (US)

(72) Inventors: Eric Linder, Columbus, OH (US); Brion Daffinson, Marietta, GA (US)

(73) Assignee: Curiteva, Inc., Tanner, AL (US)

( * ) Notice: Subject to any disclaimer, the term of this patent is extended or adjusted under 35 U.S.C. 154(b) by 0 days.

(21) Appl. No.: 17/341,841

(22) Filed: Jun. 8, 2021

(51) Int. Cl.
*A61B 17/70* (2006.01)

(52) U.S. Cl.
CPC ...... *A61B 17/7032* (2013.01); *A61B 17/7023* (2013.01); *A61B 17/7044* (2013.01)

(58) Field of Classification Search
CPC ............ A61B 17/7023; A61B 17/7032; A61B 17/7044; A61B 17/7035; A61B 17/7037
USPC ....... 606/266, 267, 268, 269, 270, 272, 278, 606/279, 306, 308, 328
See application file for complete search history.

(56) References Cited

U.S. PATENT DOCUMENTS

| | | | |
|---|---|---|---|
| 7,087,057 B2 | 8/2006 | Konieczynski et al. | |
| 7,186,255 B2 | 3/2007 | Baynham et al. | |
| 7,377,923 B2 | 5/2008 | Purcell et al. | |
| 7,833,251 B1 | 11/2010 | Ahlgren et al. | |
| 7,942,909 B2 | 5/2011 | Hammill et al. | |
| 8,038,701 B2 | 10/2011 | Rock et al. | |
| 8,337,530 B2 | 12/2012 | Hestad et al. | |
| 8,444,681 B2 | 5/2013 | Jackson et al. | |
| 8,603,145 B2 | 12/2013 | Forton et al. | |
| 8,734,495 B2 | 5/2014 | Black | |
| 9,907,574 B2 | 3/2018 | Jackson et al. | |
| 9,999,447 B2 | 6/2018 | Nichols et al. | |
| 10,034,691 B1 | 7/2018 | Lish | |
| 10,179,010 B2 | 1/2019 | Jackson et al. | |
| 10,478,225 B2 | 11/2019 | Jackson et al. | |
| 10,603,082 B2 | 3/2020 | Lish | |
| 10,610,265 B1 | 4/2020 | Ark et al. | |
| 2006/0235392 A1* | 10/2006 | Hammer | A61B 17/7034 606/264 |
| 2008/0161853 A1* | 7/2008 | Arnold | A61B 17/7005 606/246 |
| 2012/0046700 A1 | 2/2012 | Jackson et al. | |
| 2012/0059426 A1* | 3/2012 | Jackson | A61B 17/7037 606/300 |
| 2013/0060293 A1* | 3/2013 | Jackson | A61B 17/8605 606/305 |
| 2004/0321945 | 10/2014 | Black | |

(Continued)

*Primary Examiner* — Eduardo C Robert
*Assistant Examiner* — David C Comstock
(74) *Attorney, Agent, or Firm* — David L. King

(57) ABSTRACT

A modular head polyaxial pedicle screw assembly has a pedicle bone screw, a tulip, a split locking ring and a saddle. The screw has a head and a threaded shank. The split locking ring has a split ring body with one or more positioning tabs extending from a first surface of the split ring body. The split ring locking ring is configured to be placed internal of the tulip positioned in a recess, groove or undercut of an inner surface of the tulip. Upon assembly of the pedicle screw into the tulip, at least a maximum diameter of the head is positioned above the recess, groove or undercut allowing the split locking ring to be inserted into the recess or groove thereby securing the pedicle screw inside the tulip wherein the head of the pedicle screw abuts the one or more positioning tabs.

19 Claims, 14 Drawing Sheets

(56) References Cited

U.S. PATENT DOCUMENTS

| | | | | |
|---|---|---|---|---|
| 2015/0196337 A1* | 7/2015 | Biedermann | ...... | A61B 17/7032 |
| | | | | 606/305 |
| 2016/0166288 A1* | 6/2016 | Biedermann | ...... | A61B 17/7032 |
| | | | | 606/266 |
| 2017/0020573 A1* | 1/2017 | Cain | ................... | A61B 17/7037 |
| 2017/0202581 A1* | 7/2017 | Barrus | ............... | A61B 17/8685 |
| 2019/0357945 A1* | 11/2019 | Jackson | ............... | A61B 17/702 |

\* cited by examiner

MODULAR POLYAXIAL PEDICLE SCREW ASSEMBLY WITH SPLIT RING

TECHNICAL FIELD

The present invention relates to an improved modular head polyaxial pedicle screw assembly with a split ring.

BACKGROUND OF THE INVENTION

Bone anchor screws come in a variety of shapes and sizes. One of the more common styles has a polyaxial head that allows for the screw to enter the bone structure at an ideal or preferred inclination. To achieve this polyaxial inclination, the head has a shape configured to rotate about its lower external surface. This lower surface can be one of a number of shapes like conical or spherical or hemispherical. This ability is often used in devices having a modular head assembly.

The modular head polyaxial pedicle screw assembly generally includes a tulip. A tulip is a body structure having two opposing sides spaced by a slotted opening to receive a spinal rod. The tulip often employs internal threads to receive a rod locking set screw to anchor or fix the rod in the tulip. The lower portion of the tulip has an opening to receive the pedicle screw in a base seat. Often, the tulip can have a saddle that both supports the rod along an underside of the rod. The saddle having an upper recessed curvature into which the rod sits and a lower cup like opening to receive the top of the pedicle screw head. When the saddle and rod and set screw are tightened, the screw angle is fixed against the tulip seat.

Sometimes, it is preferred that the pedicle screw is first placed securely in the bone structure leaving the head protruding above the bone surface. In this surgical procedure the tulip assembly must be adapted to fit down onto the projecting screw head. To accomplish this, the surgeon must push the tulip onto and over the screw head without a clear path of vision. Accordingly, the placement must be accomplished without any way of knowing if the tulip or other device is properly secured. Thereafter, the device is tightened to complete the assembly and the only way to ensure the assembly is secure requires an upward pulling of the tightened assembly. This is not a good test as the assembly can be loosened or the screw to bone interface weakened.

A number of pedicle screw assemblies accordingly avoid providing this feature and have the pedicle screw held in the tulip prior to fixing the screw into bone.

SUMMARY OF THE INVENTION

A modular head polyaxial pedicle screw assembly has a pedicle bone screw, a tulip, a split locking ring and a saddle. The screw has a head and a threaded shank. The split locking ring has a split ring body with one or more positioning tabs extending from a first surface of the split ring body. The split locking ring is configured to be placed internal of the tulip positioned in a recess, groove or undercut of an inner surface of the tulip. The saddle has a proximal end for engaging a rod and a distal end for receiving the head of the bone screw. The saddle has an exterior surface positioned between the ends. The saddle surface is sized to move axially inside the tulip. Upon assembly of the pedicle screw into the tulip, at least a maximum diameter of the head is positioned above the recess, groove or undercut allowing the split locking ring to be inserted into the recess or groove thereby securing the pedicle screw inside the tulip wherein the head of the pedicle screw abuts the one or more positioning tabs of the split ring. The head of the pedicle screw has a driving feature for torsionally driving the pedicle screw into bone.

The saddle, when placed on the screw head, further prevents the pedicle bone screw from dislodging. The distal end of the tulip has a distal opening for receiving the pedicle screw, the distal opening preferably has a conical surface tapering inwardly from the distal end of the tulip. The outer diameter of the split locking ring is larger than a distal opening of the tulip. The bone screw has one of the following head shapes; at least partially a hemispherical or spherical head, conical or a radial array or loci of cylindrical surfaces or any other bulbous head. The recess, groove or undercut of the tulip has a distal base for supporting the split locking ring. The recess, groove or undercut has an annular wall extending from the distal base to a proximal end of the recess, groove or undercut. The annular wall extends from the distal base a distance (d), the distance (d) being at least equal to or greater than the thickness of the split ring body. The split ring body has an inner diameter having an inner surface wall of a complementary shape to the screw head. The inner surface wall is configured to hold the screw head.

The split ring body has an outer diameter having an outer surface wall. The outer surface wall has one or more flexure portions. Each flexure portion is a flat wall having reduced cross-sectional thickness measured from the inner wall toward the flat wall as compared to cross sectional thickness at the outer surface wall measured at the outer diameter. The split locking ring has a split gap opening and the one or more flexure portions are located opposed to the split gap opening. Each positioning tab has an inner wall extending from the split ring body. The inner wall of each positioning tab has a shape complementary to a lower half of the screw head of the pedicle screw and is configured to frictionally maintain the angular orientation of the tulip with respect to the pedicle screw. Each positioning tab is configured to bend or flex upon the screw head after assembly to the tulip. The force acting upon the screw head by the positioning tab is increased or decreased based on the number of the positioning tabs and the degree of angulation of the bend or flex upon the screw head after assembly into the tulip.

In one embodiment, the split locking ring has six or more positioning tabs. In another embodiment, the split locking ring has ten positioning tabs. In another embodiment, the split ring has four or more flexure portions.

BRIEF DESCRIPTION OF THE DRAWINGS

The invention will be described by way of example and with reference to the accompanying drawings in which.

DETAILED DESCRIPTION OF THE INVENTION

Figure 1:
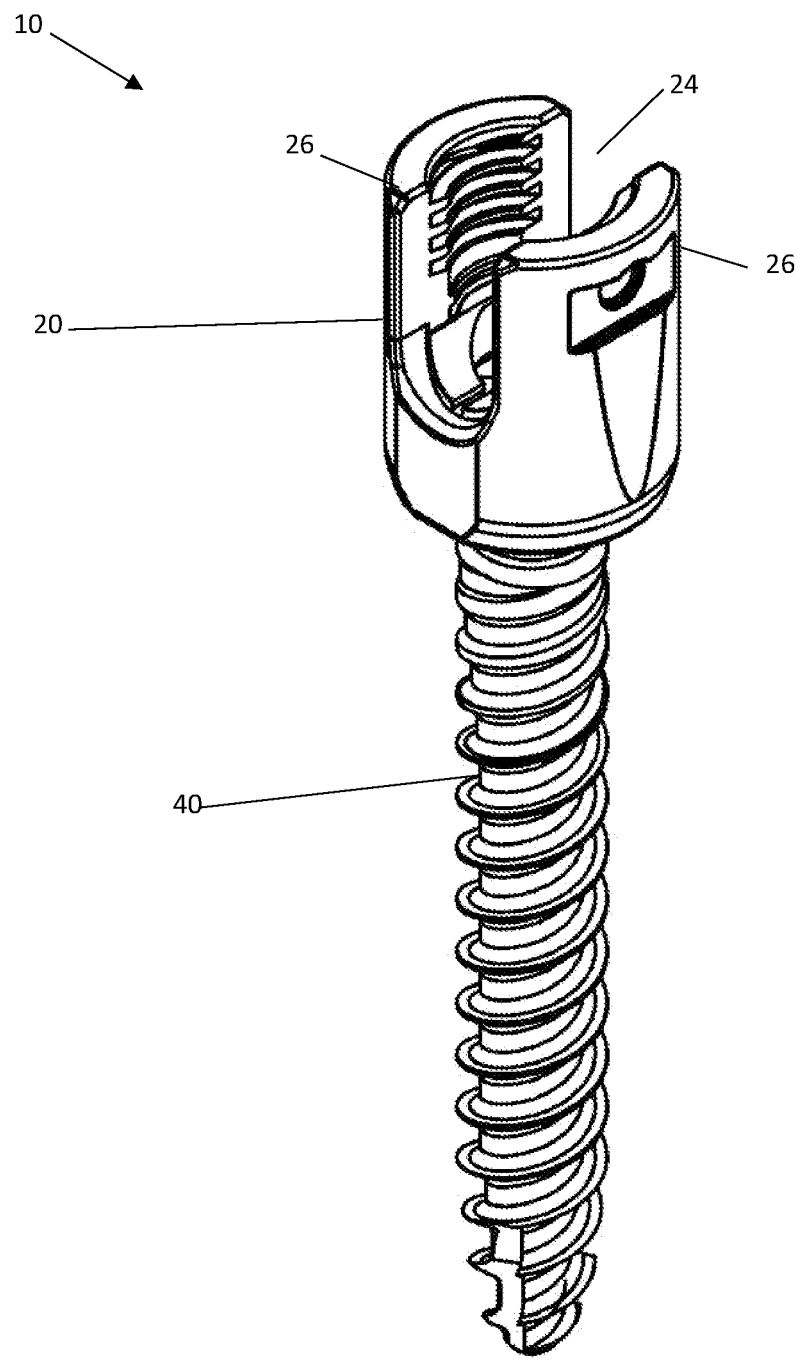
FIG. 1 is a perspective view showing the pedicle bone screw assembled to the tulip.
Figure 2:
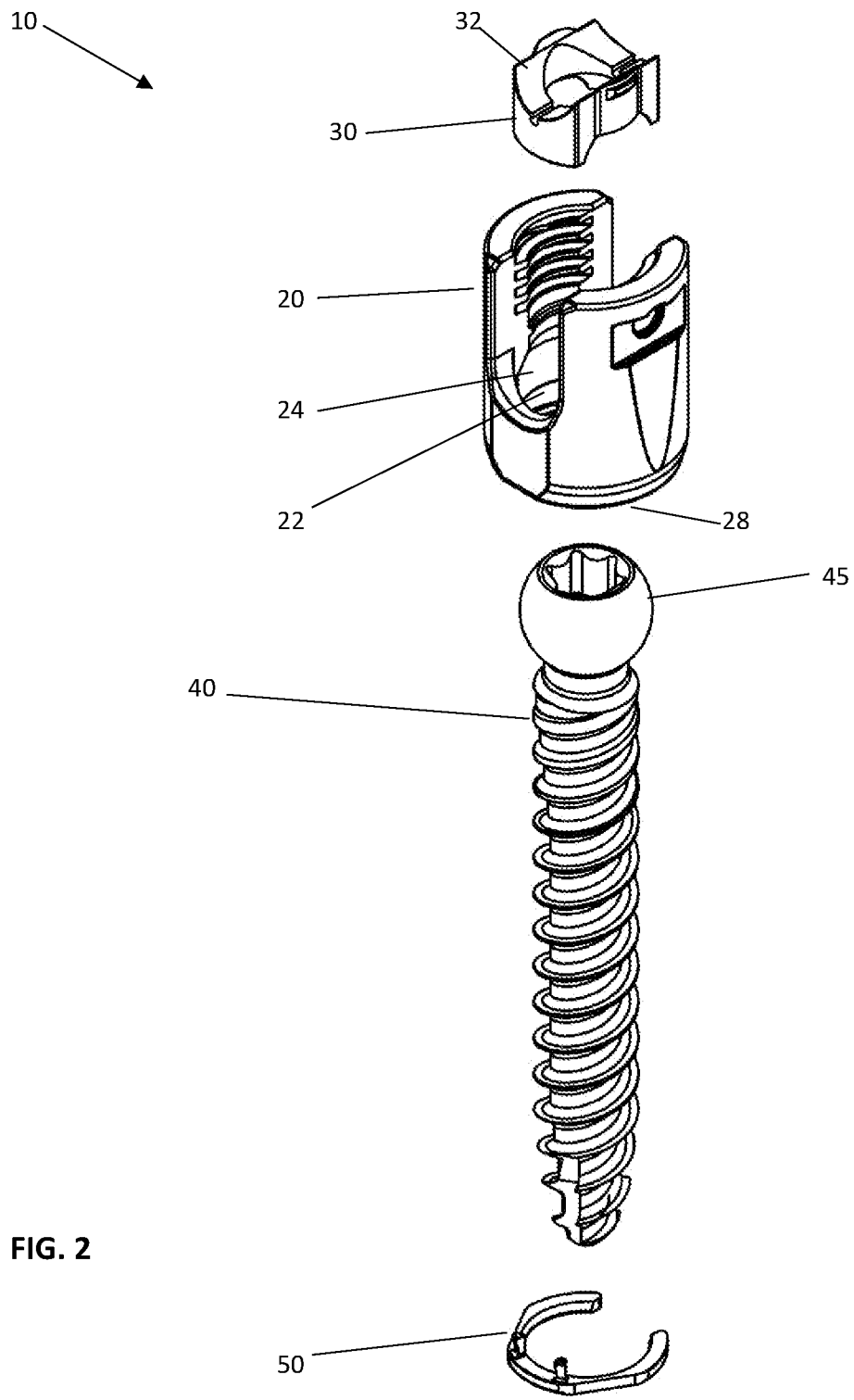
FIG. 2 is an exploded perspective view of the assembly showing the saddle, the tulip, the pedicle screw and the split locking ring.
Figure 5:
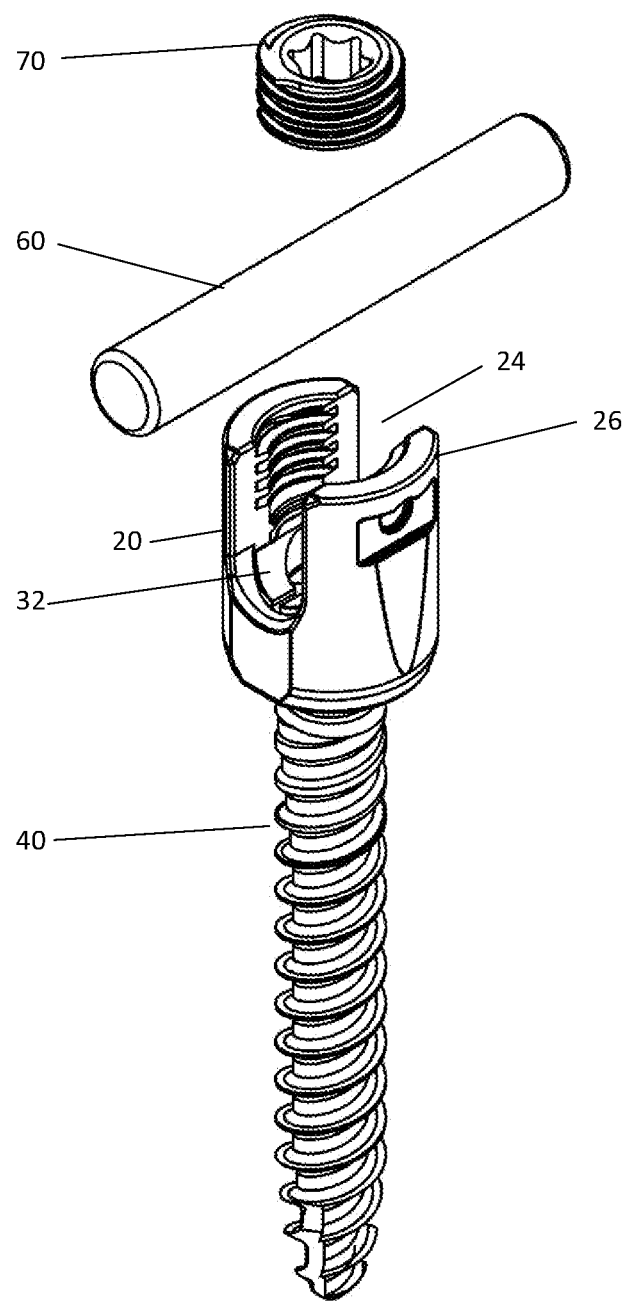
FIG. 5 is an exploded perspective view of the assembly of the pedicle screw, tulip, saddle, split locking ring and a spinal rod and a set screw.

With reference to FIGS. 1-4 views of a modular head polyaxial pedicle screw assembly 10 is illustrated. The modular head polyaxial pedicle screw assembly 10 has a bone screw 40, a tulip 20 and a split locking ring 50 internal of the tulip 20 positioned in a recess 22 of an inner surface of the tulip 20. The assembly 10 further includes a saddle 30 having a proximal end concave surface 32 for engaging a rod 60 held in place by a set screw 70 and a distal end 35 for receiving a bone screw 40. As shown in the exploded view of FIG. 2, the saddle 30 has a proximal end with a concave curvature 32, the concave curvature 32 is configured to receive a rod 60. This rod 60 is best illustrated in FIG. 5. The rod 60 shown in FIG. 5 rests upon the concave surface 32 of the saddle 30. The concave surface 32 of the saddle 30 is oriented in such a fashion that it aligns with the slotted opening 24 in the tulip 20 between the opposed walls 26 of the tulip 20. As illustrated in FIG. 2 the saddle 30 is constructed to fit through a proximal end of the tulip 20 inwardly to a lower distal portion of the tulip 20 where it resides. The saddle 30 can be inserted into the tulip 20 through a distal end opening 28 and abuts an annular stop 23. The saddle 30 has a stepped annular projection 33 fitting snugly against an interior surface of the tulip 20, the stepped projection 33 abuts the stop 23 on assembly. The stepped projection 33 has a conical or cam like surface that allows the saddle 30 to be inserted from the proximal end of the tulip 20 and pressed past the stop 23 on assembly if desired. The concave surface 32 is functionally aligned with the bottom of the slotted opening 24 of the tulip 20. This ensures that the rod 60, tulip 20 and saddle 30 are configured such that when assembled the rod 60 is oriented by both the concave surface 32 of the saddle 30 and the slotted opening 24 of the tulip 20.

Figure 7:
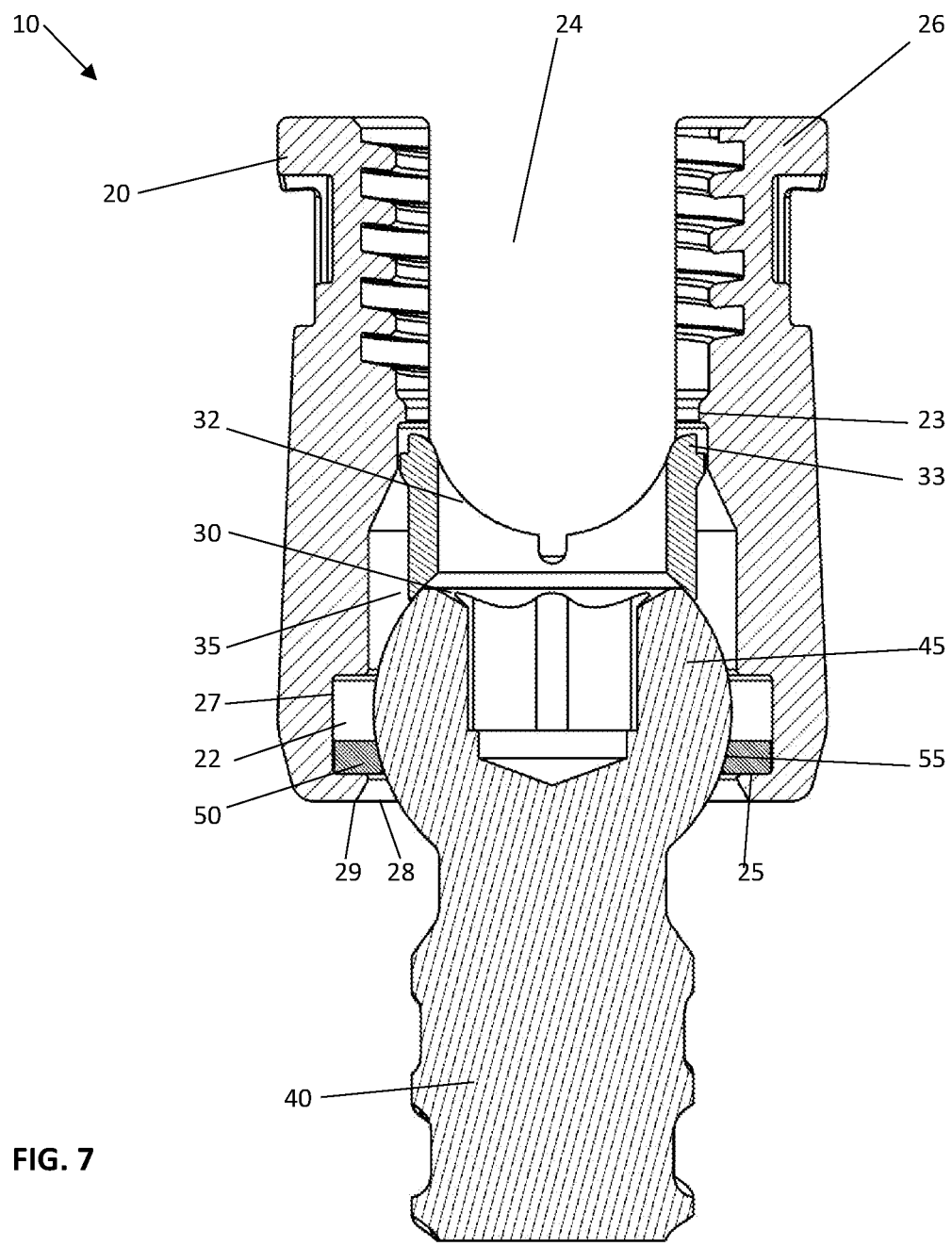
FIG. 7 is a cross sectional view of the assembly not taken through a positioning tab showing the saddle and the pedicle screw held in the tulip by the split locking ring.

As further shown in FIG. 2, the assembly 10 includes a split locking ring 50. The split locking ring 50 shown in the lower distal portion of FIG. 2 is designed to fit into a distal end of the tulip 20. The distal end of the tulip 20 has an opening 28 with a conical surface 29. The split locking ring 50 is configured to enter into this distal opening 28 and fit in a recess or groove 22 of the tulip 20. This is best illustrated in FIG. 7 wherein the split locking ring 50 is positioned within the recess 22 and holds the screw head 45 below the maximum diameter of the screw head 45 or a distal lower portion of the screw head 45 which is engaged by an internal diameter of the split locking ring 50. The internal diameter inner surface wall 55 is configured to complementarily fit the shape of the screw head 45. As shown in FIG. 2, the screw head 45 is hemispherical and accordingly, the split locking ring 50 will have a hemispherical shape to complimentarily fit the screw head 45. As further illustrated, the saddle 30 is shown positioned at the proximal end of the screw head 45 in FIG. 7.

The recess or groove 22 has an diameter larger than the split locking ring to allow for expansion of the split locking ring into the recess or groove. The compressed split locking ring 50 will enter into the distal opening 28 of the tulip 20, upon release, the split locking ring 50 expands and abuts against the exterior walls 27 of the recess or groove 22. The recess or groove 22 allows the screw 40 being held and supported by the split locking ring 50 to polyaxially move. As shown in FIG. 7, the split locking ring 50 sits on a ledge or base 25 of the tulip 20. The base 25 is the lower or distal portion of the recess 22 and the opening includes a conical surface 29 at the distal end of the tulip 20.

Figure 6:
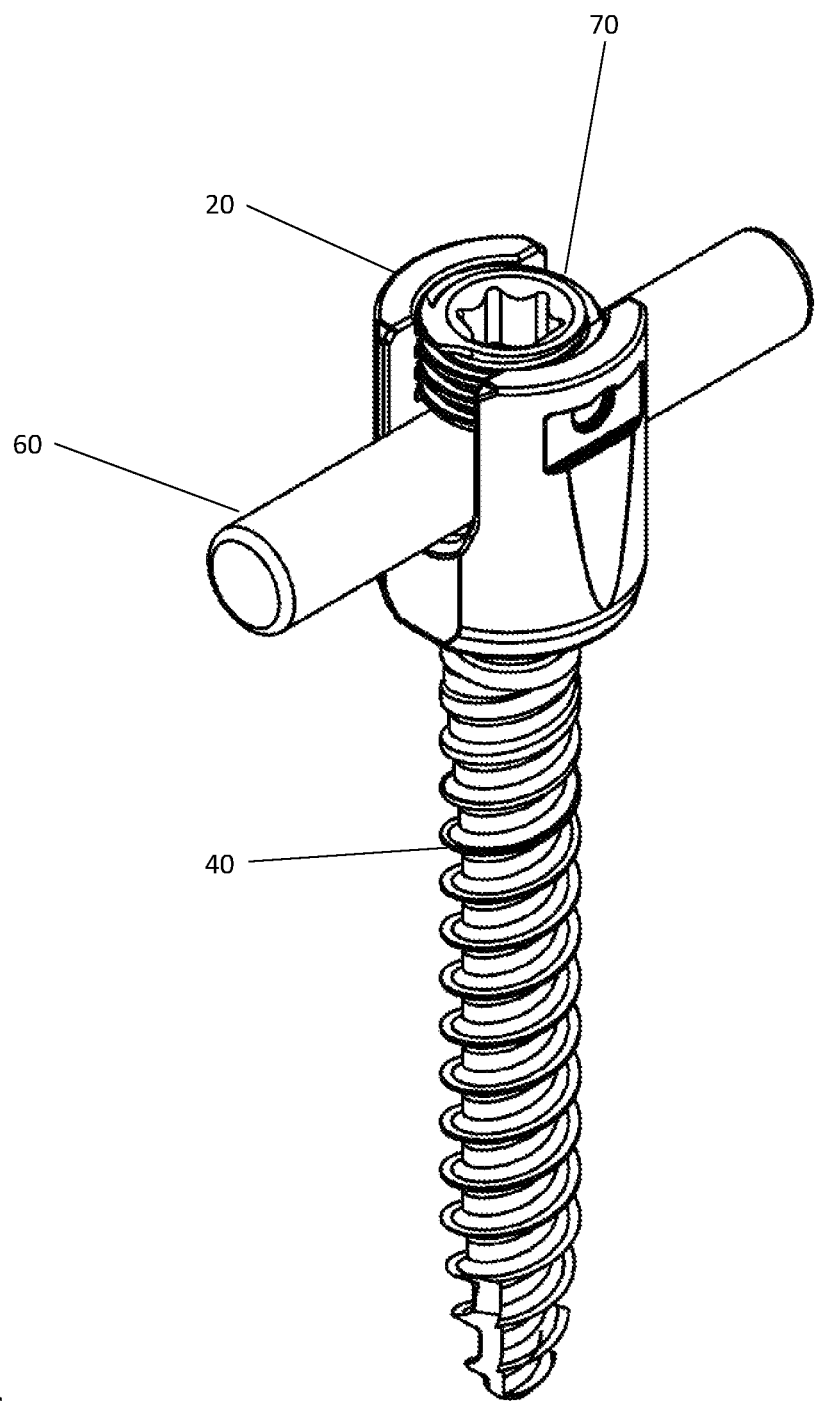
FIG. 6 is a perspective view of the assembly showing the spinal rod held in the tulip assembly by the set screw.

As shown in FIG. 6, once the pedicle screw 40, saddle 30 and split locking ring 50 are in position inside the tulip 20, the rod 60 can be positioned in such a fashion that it aligns with the concave surface 32 of the saddle 30 through the slotted opening 24 of the tulip 20. Thereafter, a set screw 70 can be inserted into the tulip 20 and threadingly engage the walls 26 on either side of the tulip 20. As the set screw 70 is tightened, the rod 60 pushes against the concave surface 32 of the saddle 30 and as the concave surface 32 of the saddle 30 is engaged, the tulip 20 moves relative to the saddle 30 in such a way that the assembly tightens the pedicle screw head 45 firmly against the split locking ring 50. The split locking ring 50 fully supports and engages the lower hemispherical half of the screw head 45 at the internal diameter inner surface wall 55 shown in FIG. 7.

As shown in all the embodiments, the screw head 45 is hemispherical. Alternatively, it can be conical or some other bulbous shape as long as the split locking ring 50 has a complementary surface wall 55 to receive the lower or distal half of the screw head 45.

Figure 8:
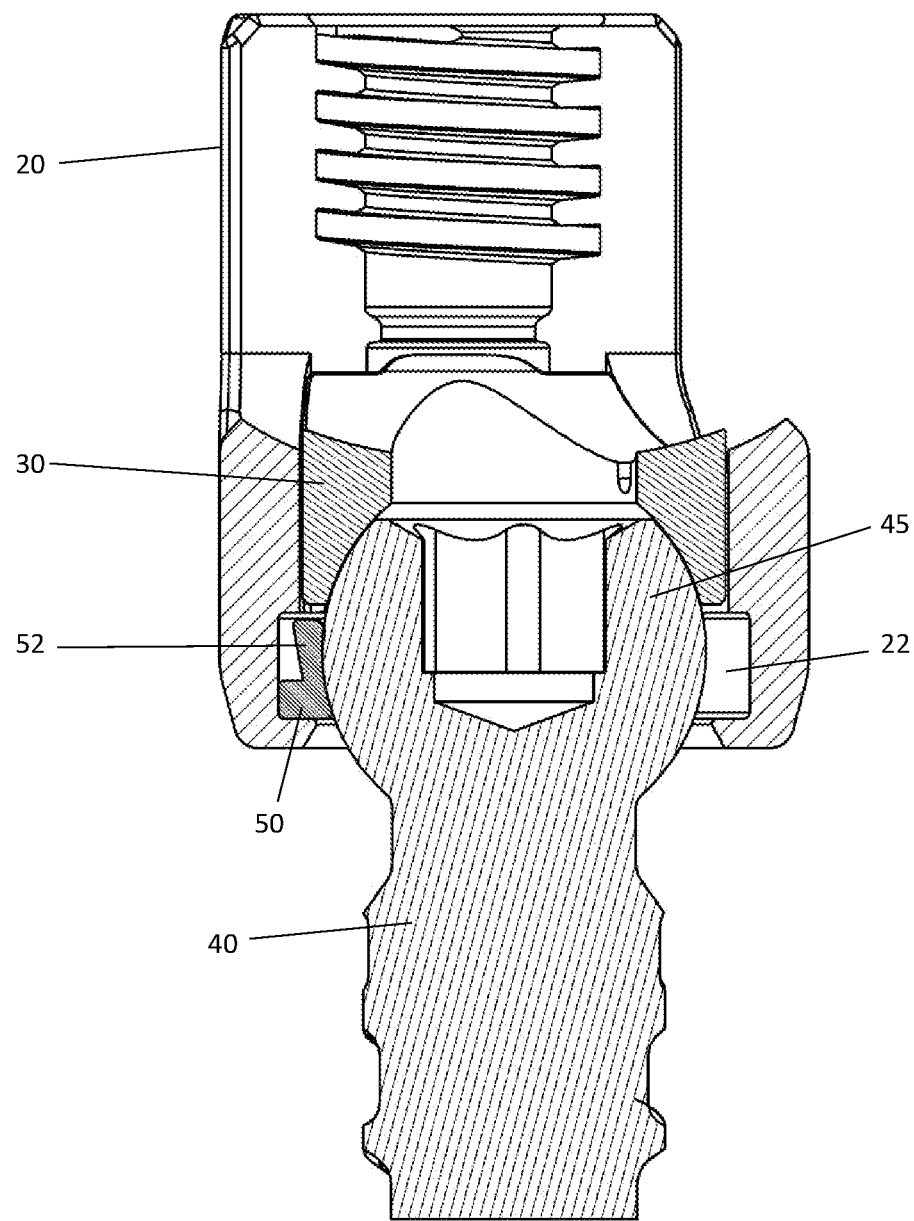
FIG. 8 is a cross sectional view of the assembly taken through a positioning tab showing the interface of the positioning tab and the screw head.

FIG. 8 is a second cross sectional view of the tulip 20 with the saddle 30 showing a positioning tab or appendage 52 that extends from a proximal exterior surface 53 of the split locking ring 50. This positioning tab 52 also engages the screw head 45 as illustrated by bending or flexing to apply force to the screw head 45. As shown, the cross-sectional view of FIG. 8 is cut through the slotted opening 24 of the tulip 20 to show this position.

Figure 9:
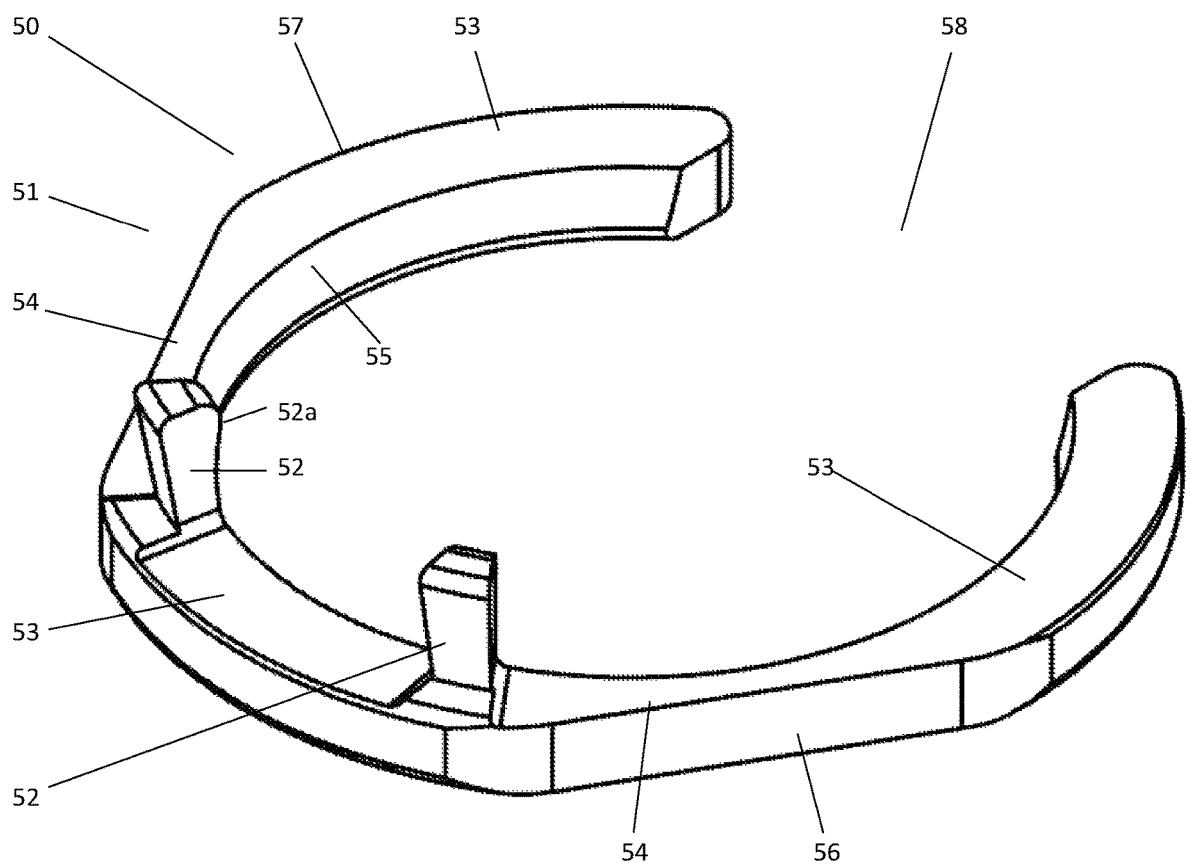
FIG. 9 is a perspective view of the split locking ring of a first embodiment with two positioning tabs and two flexure portions.
Figure 10:
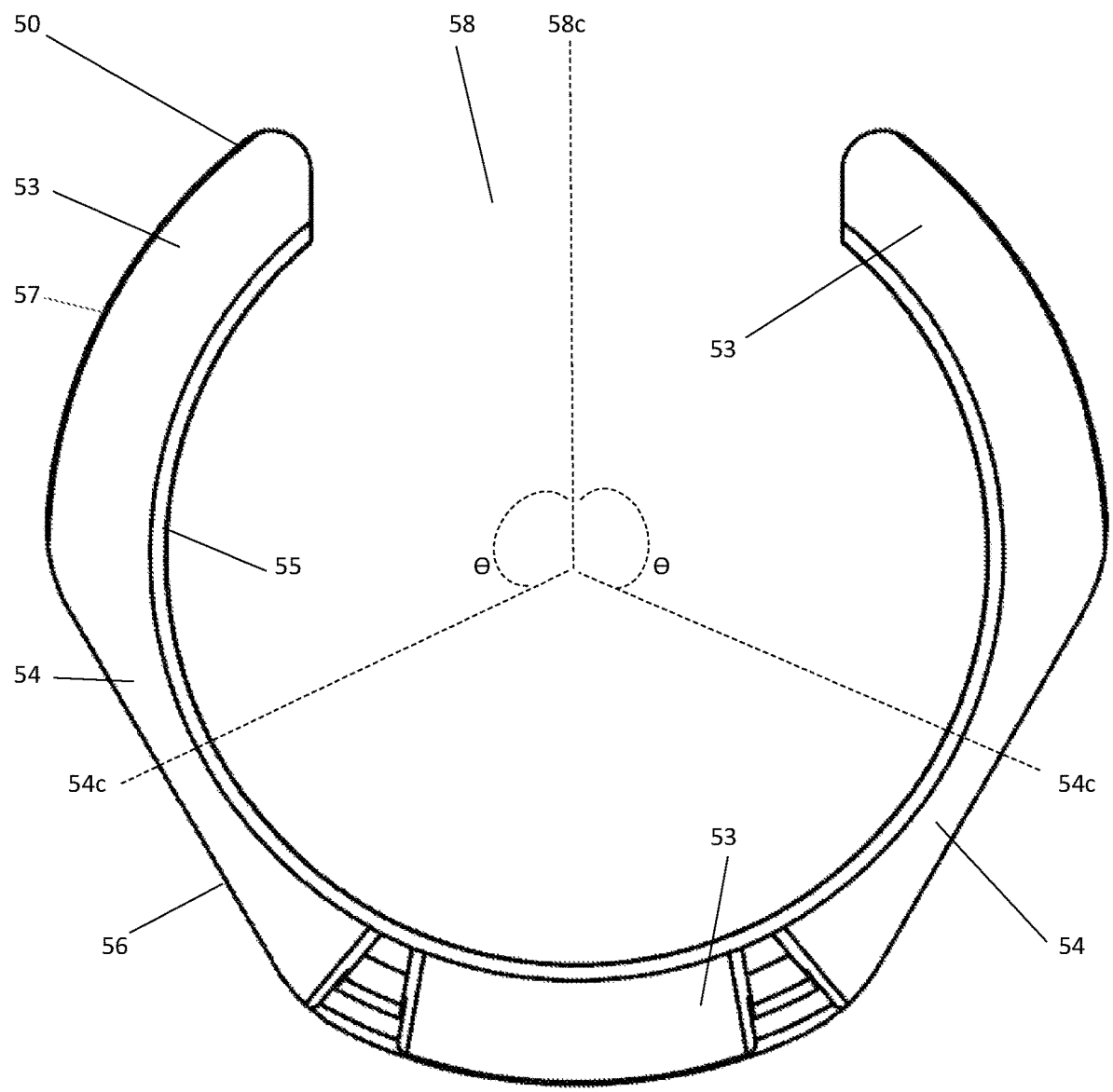
FIG. 10 is a top plan view of the split locking ring with two positioning tabs and two flexure portions taken from FIG. 9.

FIGS. 9 and 10 best illustrate a first embodiment of the unique split locking ring 50 of the present invention. In this first embodiment, the split locking ring 50 has a gap opening 58 between the split ring body 51. In the unattached or free state, the outer diameter of the split locking ring 50 is larger than the distal opening 28 of the tulip 20. This is important because when the compressed split locking ring 50 is positioned in the recess 22 on assembly then released and relaxed such that the relaxed diameter pushes against the exterior wall 27 of the of the recess or groove 22 and rests flat on the base 25 of the tulip 20 such that it can provide the necessary support for the screw head 45. As shown in the first embodiment, split locking ring 50 has a split ring body 51 with two or more fingers 52 extending from a first surface of the split ring body 51. The split locking ring 50 being internal of the tulip 20 positioned in the recess or groove 22 of the inner surface of the tulip 20. The split ring body 51 has an inner diameter having an inner surface wall 55 of a complimentary shape of the screw head 45. The inner surface wall 55 is configured to hold the screw head 45. The split ring body 51 has an outer diameter having an outer surface wall 57. The outer surface wall 57 has a pair of flexure portions 54. The flexure portions 54 are flat walls 56 having a reduced cross-sectional thickness measured from the inner surface wall 55 toward the flat wall 56 compared to the outer surface wall 57 measured at the outer diameter of the split ring body 51. The split ring body 51 further has a gap opening 58. The gap opening 58 is a space between the ends of the split ring body 51 and is effectively a cut out so the annular shape of the split locking ring 50 can be reduced allowing the split locking ring 50 to move and flex inwardly at the two flexure portions to facilitate assembly into the tulip 20. The gap opening 58 is positioned such that the pair of flexure portions 54 are located opposed to the gap opening 58.

Figure 3:
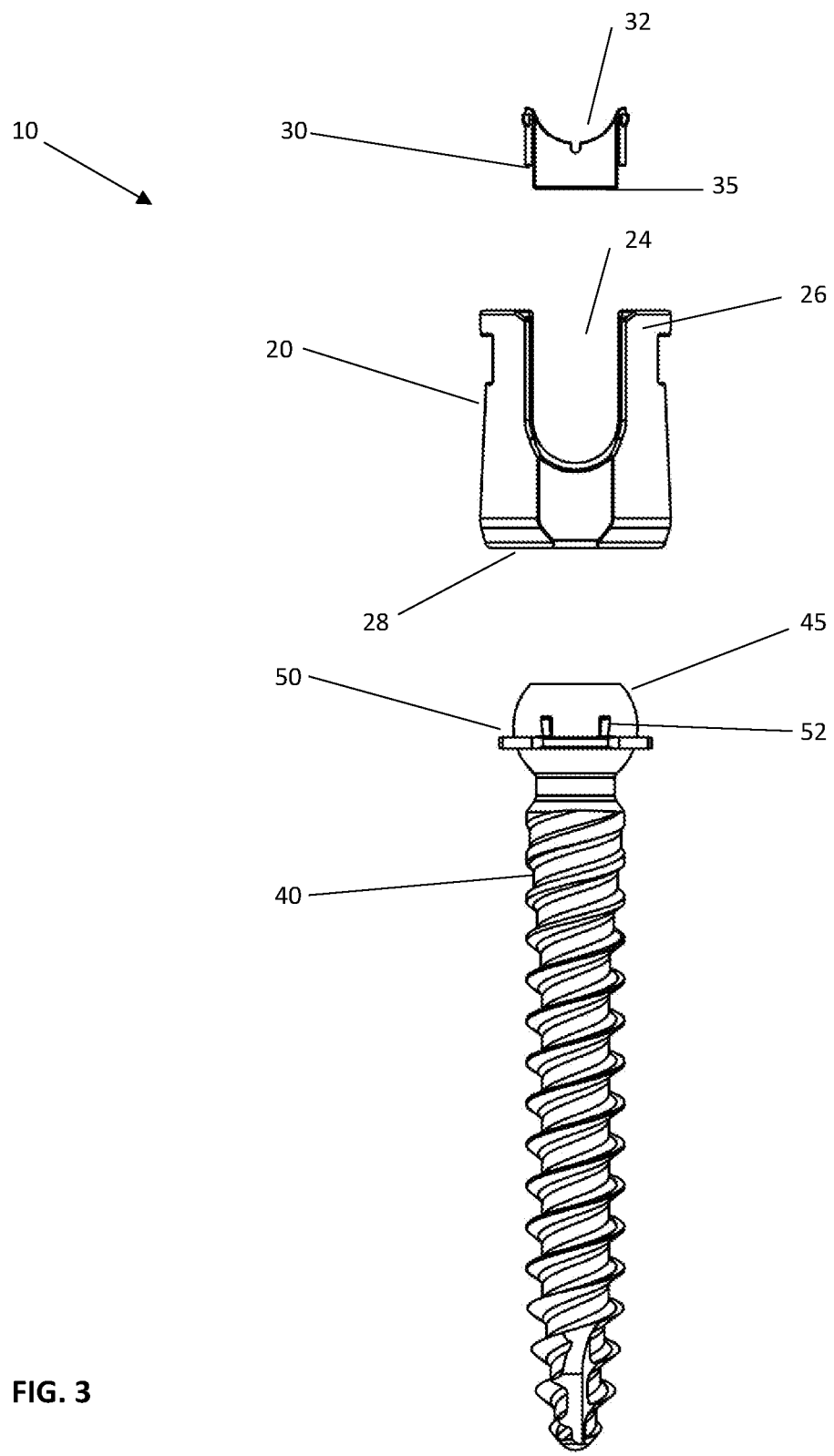
FIG. 3 is an exploded side view of the assembly showing the saddle, the tulip, and the location of the split locking ring with respect to the pedicle screw after assembly.
Figure 4:
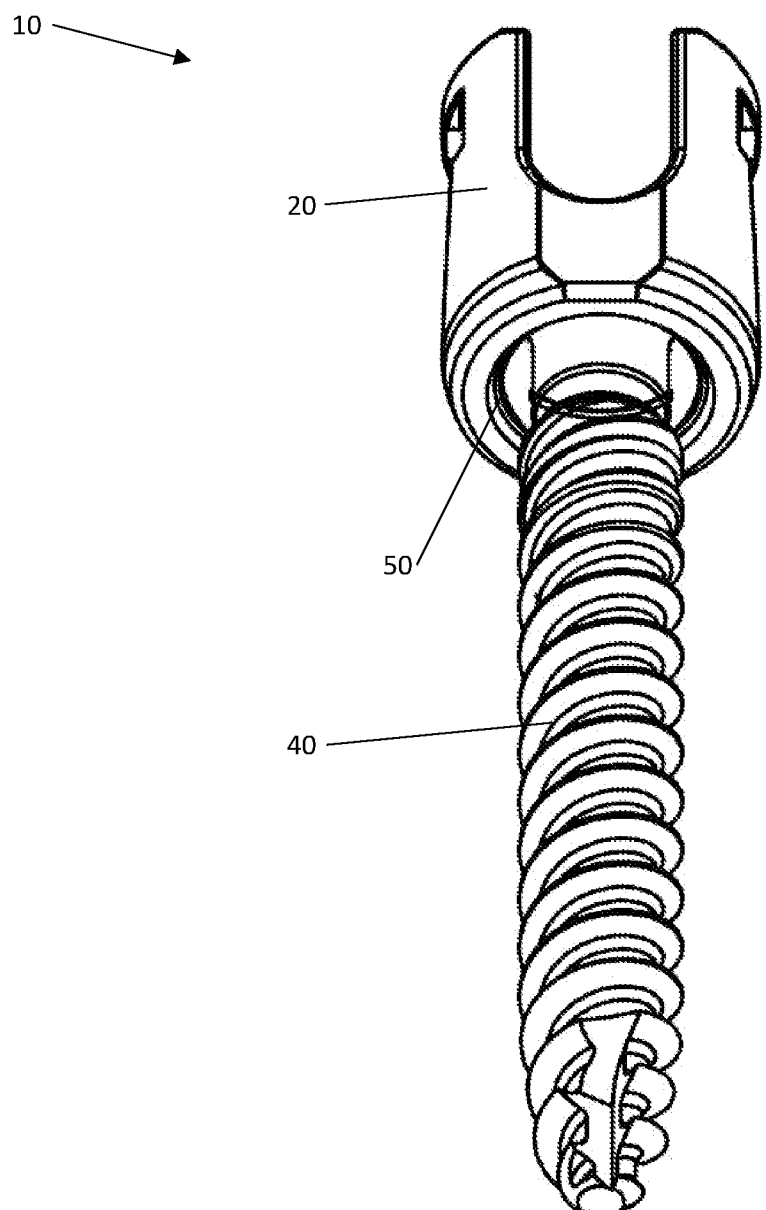
FIG. 4 is a lower perspective view of the screw assembly showing the pedicle screw seated in the tulip with the split locking ring fully seated in the groove of the tulip.

As further shown in FIGS. 9 and 10, the flexure portions 54 and the gap 58 each have centers 54c and 58c that are symmetrically spaced at an angle θ of about 120 degrees apart. As further shown, at the exterior top surface 53 of the split ring body 51 are a pair of positioning tabs 52, the positioning tabs 52 protrude and extend outwardly from this surface 53. The positioning tabs 52 are aligned with the inner diameter or inner surface wall 55 and have a curvature that is complementary to the hemispherical curvature of the screw head 45. This positioning tab 52 curvature at the proximal extreme 52a extends some distance inwardly of the inner diameter. This is an important feature because on assembly to the screw head 45, these positioning tabs 52 are configured to flex and bend outwardly and provide a force on the outer surface of the screw head 45. This is illustrated in FIG. 3 where the split locking ring 50 is shown simply attached to the hemispherical screw head 45.

Figure 11:
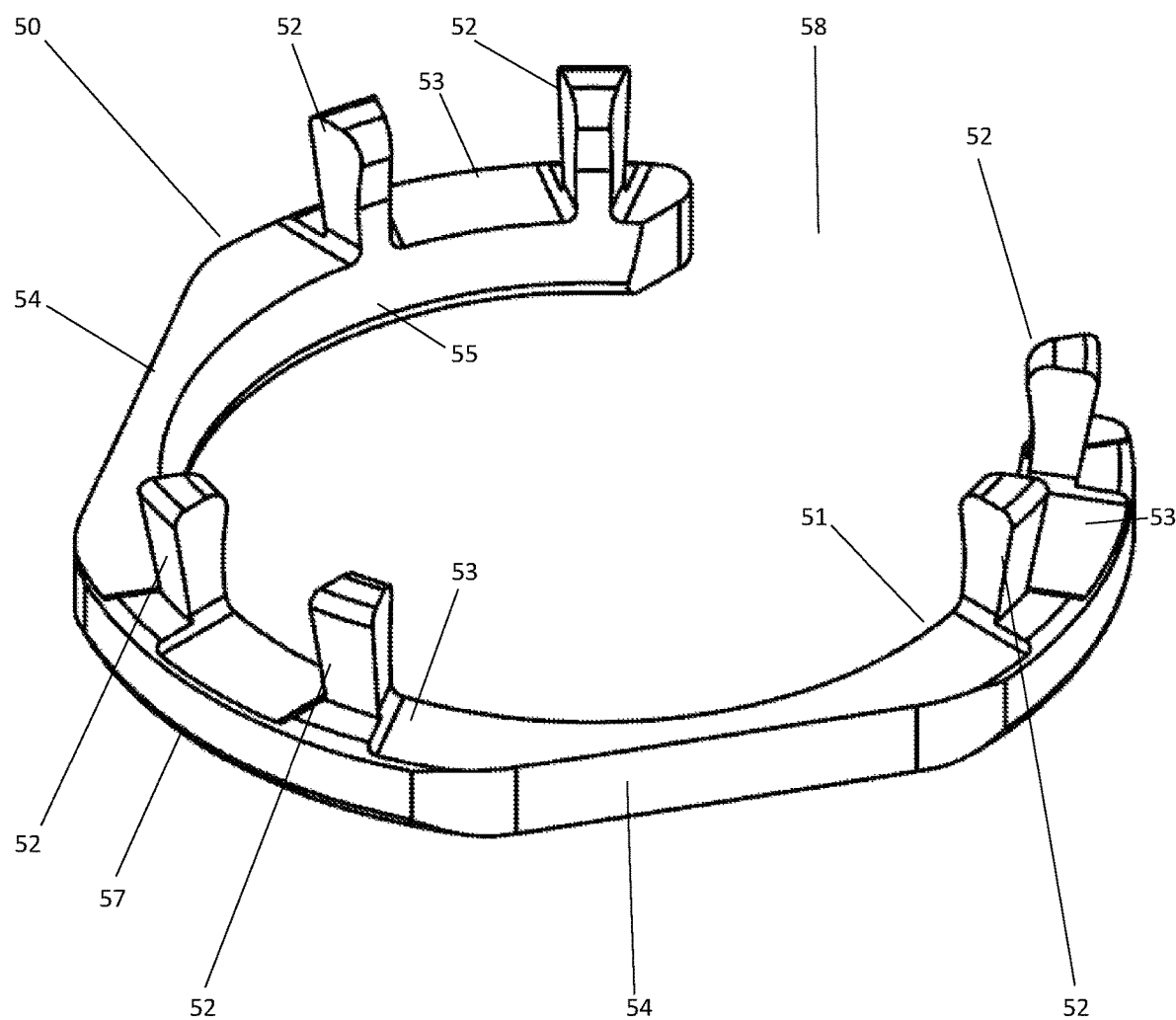
FIG. 11 is a perspective view of an alternative split locking ring of a second embodiment with six positioning tabs and two flexure portions.
Figure 12:
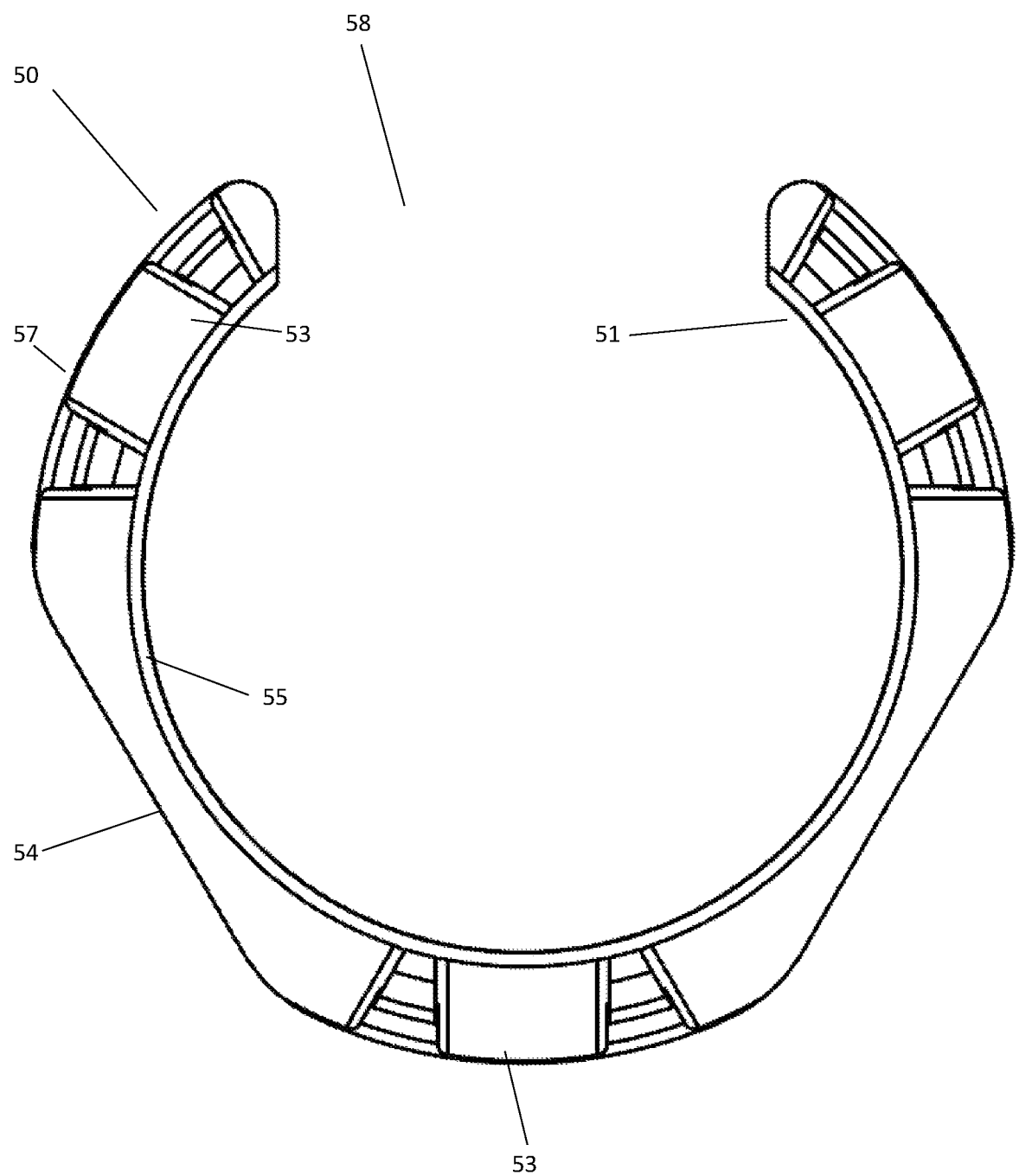
FIG. 12 is a top plan view of the alternative split locking ring with six positioning tabs and two flexure portions taken from FIG. 11.

In a second embodiment illustrated in FIGS. 11 and 12, the split locking ring 50 has all the features previously mentioned, however additional positioning tabs 52 are provided. Accordingly, one or more positioning tabs 52 are provided on each side of the split locking ring 50 near the gap opening 58. This provides six positioning tabs 52 projecting outwardly from the exterior surface and more complimentarily fits the screw head 45 on assembly. This view of FIGS. 11 and 12 shows the positioning of the positioning tabs 52 about the split ring body 51.

Figure 13:
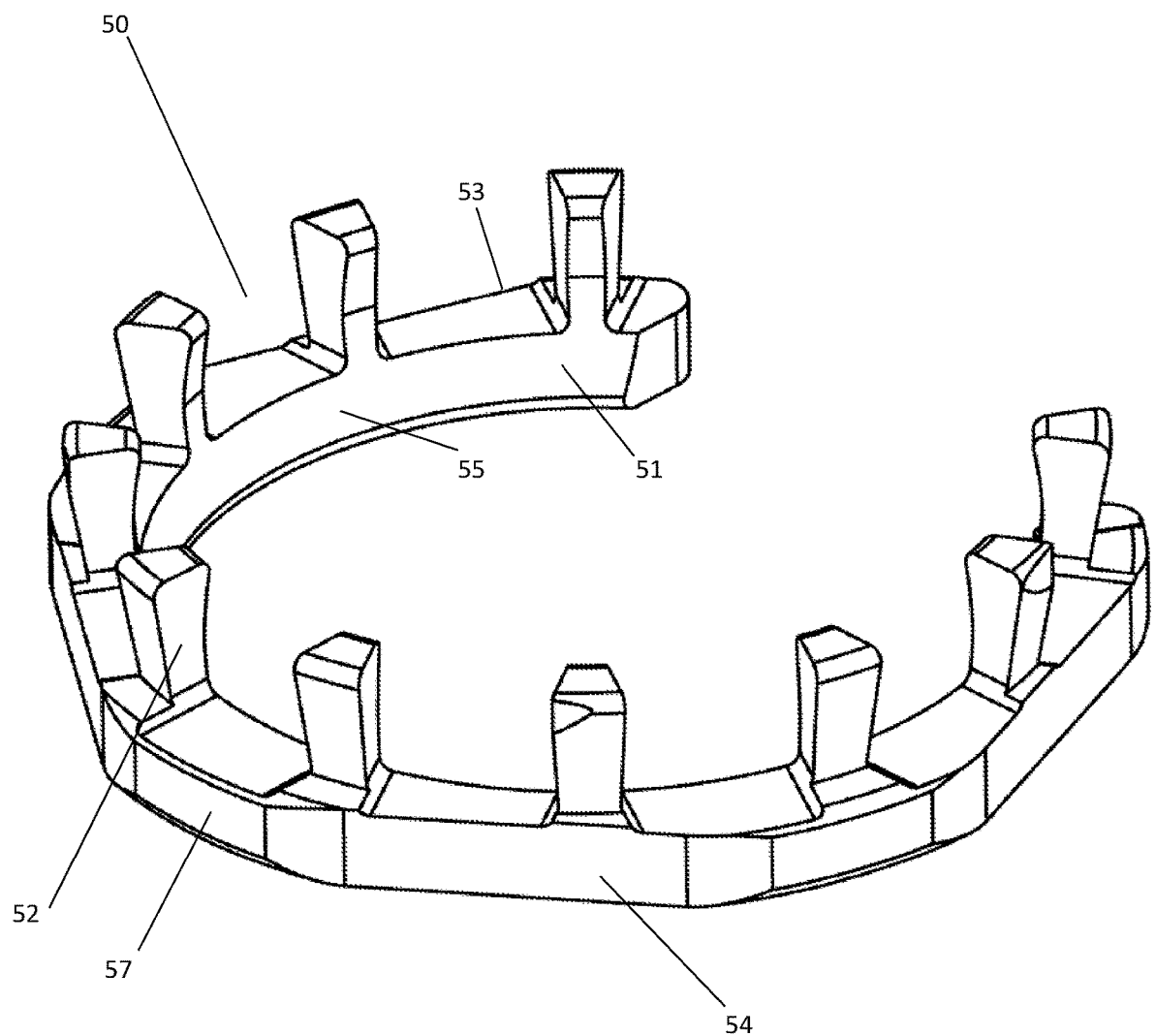
FIG. 13 is a perspective view of an alternative split locking ring of a third embodiment with ten positioning tabs and four flexure portions.
Figure 14:
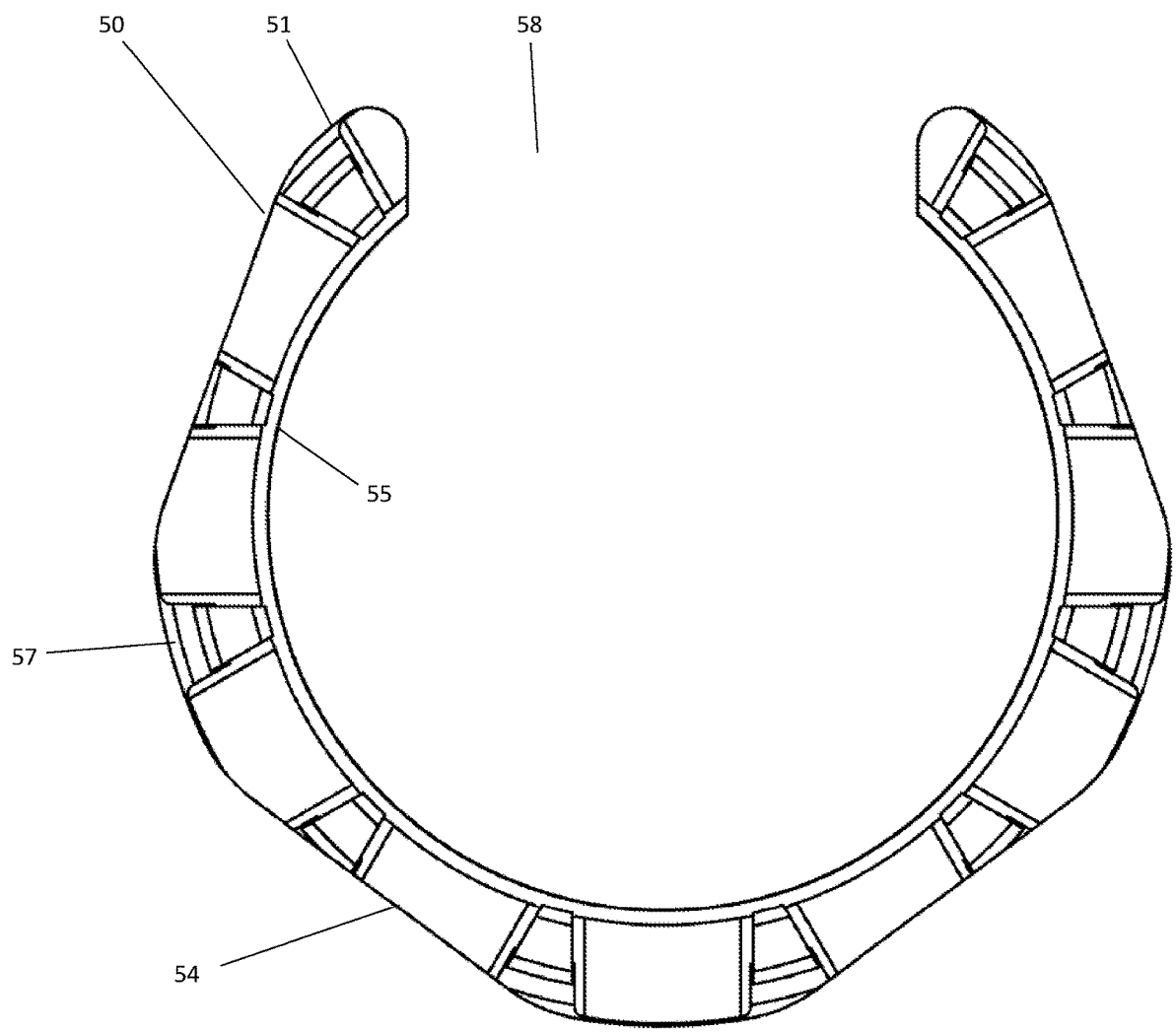
FIG. 14 is a top plan view of the alternative split locking ring with ten positioning tabs and four flexure portions taken from FIG. 13.

In a third embodiment shown in FIGS. 13 and 14, there are ten positioning tabs 52 positioned about the split locking ring 50 providing even more contact and support for the screw head 45 on assembly and four flexure portions 54 to further facilitate assembly.

It is important to note that any of the split locking ring 50 embodiments shown in these views can be used in the assembly views of FIGS. 1-8. Upon assembly of the rod 60 into the tulip 20 tightening the set screw 70 into the tulip presses the rod 60 against the saddle 30 thereby causing the tulip 20 to pull upwardly relative to the saddle 30 which tightens the split locking ring 50 and its associated positioning tabs 52 snugly against the screw head 45. Upon assembly, the screw head 45 is configured to be held only by the split locking ring 50 which in turn is held by the base and the tulip 20. As the tightening occurs, the ability of the polyaxial screw 40 and the tulip 20 to move relative to each other is limited by the gripping force created by the tightening of the split locking ring 50 against the screw head 45. Upon assembly, however, due to the use of one or more positioning tabs 52, it is possible that prior to inserting the rod into the tulip 20, the tulip 20 itself can be oriented relying on the positioning tabs 52 to help position the orientation of the tulip 20 relative to the bone screw. This greatly facilitates the introduction of a rod into a tulip during a procedure.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A modular head polyaxial pedicle screw assembly comprising:
   a pedicle bone screw, the screw having a head and a threaded shank;
   a tulip, the tulip having a distal end opening for receiving the head of the pedicle bone screw;
   a saddle having a proximal end for engaging a rod and a distal end for receiving the head of the bone screw;
   a split locking ring having a split ring body with two or more positioning tabs extending from a first surface of the split ring body, the split locking ring being internal of the tulip upon assembly through the distal end opening and positioned in a recess, groove or undercut of an inner surface of the tulip, wherein the split ring body has an outer diameter having an outer surface wall, the outer surface wall has two flexure portions, each flexure portion is a flat wall having reduced cross-sectional thickness measured from the inner wall toward the flat wall as compared to a cross sectional thickness at the outer surface wall measured at the outer diameter, and the split locking ring has a split gap opening with two flexure portions that are located opposed to the split gap opening and two of the two or more positioning tabs are positioned between the two flexure portions directly opposite the split gap opening located in a portion of the cross sectional thickness measured at the outer diameter, wherein a center length of each of the flat portions of the two flexure portions and a center length of the gap opening are symmetrically spaced at an angle θ of 120 degrees apart and upon assembly of the split locking ring into the tulip the split locking ring is compressed as the gap opening is reduced allowing the split locking ring to move and flex inwardly at the two flexure portions to facilitate assembly through the distal end opening of the tulip opening into the recess, groove or undercut of the tulip and upon entry past the distal end opening, the split locking ring expands wherein the outer diameter of the split ring is larger than the distal end; and
   wherein upon assembly of the pedicle bone screw into the tulip through the distal end opening and thereafter positioning the split locking ring into the recess, groove, or undercut of the tulip secures the pedicle bone screw inside the tulip wherein the head of the pedicle bone screw abuts the two or more positioning tabs.

2. The modular head polyaxial pedicle screw assembly of claim 1 wherein the saddle, when placed on the screw head, further prevents the split locking ring from dislodging.

3. The modular head polyaxial pedicle screw assembly of claim 1 wherein a distal end of the tulip has a distal opening for receiving the pedicle screw, the distal opening has a conical surface tapering inward distally.

4. The modular head polyaxial pedicle screw assembly of claim 1 wherein the outer diameter of the split locking ring is larger than a distal opening of the tulip.

5. The modular head polyaxial pedicle screw assembly of claim 1 wherein the bone screw has one of the following head shapes; at least partially a hemispherical or spherical head, conical or a radial array or loci of cylindrical surfaces or any other bulbous head.

6. The modular head polyaxial pedicle screw assembly of claim 1 wherein the recess, groove or undercut of the tulip has a distal base for supporting the split locking ring.

7. The modular head polyaxial pedicle screw assembly of claim 6 wherein the recess, groove or undercut has an annular wall extending from the distal base to a proximal end of the recess, groove or undercut.

8. The modular head polyaxial pedicle screw assembly of claim 7 wherein the annular wall extends from the distal base a distance (d), the distance (d) being equal to or greater than the thickness of the split ring body.

9. The modular head polyaxial pedicle screw assembly of claim 8 wherein the split ring body has an inner diameter having an inner surface wall of a complementary shape to the screw head, the inner surface wall configured to hold the screw head.

10. The modular head polyaxial pedicle screw assembly of claim 9 wherein each positioning tab has an inner wall extending from the split ring body, the inner wall extending from the inner diameter of the split ring body.

11. The modular head polyaxial pedicle screw assembly of claim 10 wherein the inner wall of each positioning tab has a shape complementary to a lower half of the screw head of the pedicle screw.

12. The modular head polyaxial pedicle screw assembly of claim 11 wherein each positioning tab is configured to bend or flex upon tightening the screw head to the tulip.

13. The modular head polyaxial pedicle screw assembly of claim 1 wherein the split locking ring has six or more positioning tabs.

14. The modular head polyaxial pedicle screw assembly of claim 1 wherein the split locking ring has 10 positioning tabs.

15. The modular head polyaxial pedicle screw assembly of claim 1 wherein the head has a driving feature for torsionally driving the screw into bone.

16. A modular head polyaxial pedicle screw assembly comprising:
   a pedicle bone screw, the screw having a head and a threaded shank;
   a tulip, the tulip having a distal end opening for receiving the head of the pedicle bone screw;
   a saddle having a proximal end for engaging a rod and a distal end for receiving the head of the bone screw;
   a split locking ring having a split ring body with two or more positioning tabs extending from a first surface of the split ring body, the split locking ring being internal of the tulip upon assembly through the distal end opening and positioned in a recess, groove or undercut of an inner surface of the tulip, wherein the split ring body has an outer diameter having an outer surface wall, the outer surface wall has two flexure portions, each flexure portion is a flat wall having reduced cross-sectional thickness measured from the inner wall toward the flat wall as compared to a cross sectional thickness at the outer surface wall measured at the outer diameter, and the split locking ring has a split gap opening with two flexure portions that are located opposed to the split gap opening and two of the two or more positioning tabs are positioned between the two flexure portions directly opposite the split gap opening located in a portion of the cross sectional thickness measured at the outer diameter, wherein a center length of each of the flat portions of the two flexure portions and a center length of the gap opening are symmetrically spaced at an angle θ of 120 degrees apart and upon assembly of the split locking ring into the tulip the split locking ring is compressed as the gap opening is reduced allowing the split locking ring to move and flex inwardly at the two flexure portions to facilitate assembly through the distal end opening of the tulip opening into the recess, groove or undercut of the tulip and upon entry past the distal end opening, the split locking ring expands wherein the outer diameter of the split ring is larger than the distal end; and
   wherein upon assembly of the pedicle bone screw into the tulip through the distal end opening and thereafter positioning the split locking ring into the recess, groove, or undercut of the tulip secures the pedicle bone screw inside the tulip wherein the head of the pedicle bone screw abuts the two or more positioning tabs.

17. The modular head polyaxial pedicle screw assembly of claim 16 wherein the head of the pedicle bone screw abuts the one or more positioning tabs with a force sufficient to maintain the orientation of the tulip with respect to the head of the bone screw.

18. A modular head polyaxial pedicle screw assembly comprising:
   a pedicle bone screw, the screw having a head and a threaded shank;
   a tulip, the tulip having a distal end opening for receiving the head of the pedicle bone screw;
   a saddle having a proximal end for engaging a rod and a distal end for receiving the head of the bone screw;
   a split locking ring having a split ring body with a gap opening and with one or more positioning tabs extending from a first surface of the split ring body, the split locking ring being internal of the tulip upon assembly through the distal end opening and positioned in a recess, groove or undercut of an inner surface of the tulip and upon assembly of the split locking ring into the tulip the split locking ring is compressed as the gap opening is reduced allowing the split locking ring to move and flex inwardly to facilitate assembly through the distal end opening of the tulip opening into the recess, groove or undercut of the tulip and upon entry past the distal end opening, the split locking ring expands wherein the outer diameter of the split ring is larger than the distal end opening; and
   wherein upon assembly of the pedicle bone screw into the tulip through the distal end opening and thereafter positioning the split locking ring into the recess, groove, or undercut of the tulip secures the pedicle bone screw inside the tulip wherein the head of the pedicle bone screw abuts the one or more positioning tabs.

19. The modular head polyaxial pedicle screw assembly of claim 18 wherein the head of the pedicle bone screw abuts the one or more positioning tabs with a force sufficient to maintain the orientation of the tulip with respect to the head of the bone screw.

\* \* \* \* \*